United States Patent [19]

Blind et al.

[11] Patent Number: 4,871,828

[45] Date of Patent: Oct. 3, 1989

[54] PURIFICATION/ISOLATION OF ISOCYANATE CONDENSATES

[75] Inventors: Andre Blind; Gerard Collas, both of Caluire; Jean Robin; Ferenc Sagi, both of Lyon, all of France

[73] Assignee: Rhone-Poulenc Chimie, Courbevoie, France

[21] Appl. No.: 249,305

[22] Filed: Sep. 26, 1988

[30] Foreign Application Priority Data

Sep. 24, 1987 [FR] France .................. 87/13478

[51] Int. Cl.[4] .............................................. C08G 18/82
[52] U.S. Cl. ....................................... 528/44; 528/68; 528/483; 528/490; 564/38; 560/26; 560/115; 560/158; 525/452; 525/453; 525/459; 525/460
[58] Field of Search ................. 528/44, 68, 483, 490; 564/38; 560/26, 115, 158; 525/452, 453, 459, 460

[56] References Cited

U.S. PATENT DOCUMENTS 4,649,162  3/1987  Roche et al. .................... 528/483

Primary Examiner—Maurice J. Welsh
Attorney, Agent, or Firm—Burns, Doane, Swecker & Mathis

[57] ABSTRACT

Polyisocyanates containing only trace amounts of free aromatic diisocyanates are recovered by purifying and isolating an isocyanate condensate containing free NCO groups from an impure admixture thereof, said isocyanate condensate impure admixture having been prepared by reacting a stoichiometric excess of an aromatic di- or polyisocyanate with a reactant compound containing at least two functional groups which are reactive with NCO groups, and such purification/isolation entailing extracting unreacted excess di- or polyisocyanate from said impure admixture with an inert gas, e.g., carbon dioxide, in either the liquid or supercritical state.

19 Claims, No Drawings

PURIFICATION/ISOLATION OF ISOCYANATE CONDENSATES

BACKGROUND OF THE INVENTION

1. Field of the Invention:

The present invention relates to the isolation and purification of isocyanate condensates containing free NCO groups, prepared from aromatic di- or polyisocyanates, and wherein at least one of the free NCO groups is directly bonded to an aromatic ring.

2. Description of the Prior Art:

Isocyanate condensates are used for preparing foams, elastomers, adhesives, paints and varnishes, the exceptional properties of which condensates now being well known to this art.

These condensates, which contain free NCO groups, are prepared by reacting at least one compound containing at least two functional groups reactive with isocyanates, with a molar excess of a di- or polyisocyanate, optionally in a solvent which is inert with respect to NCO groups. The compound containing functional groups which are reactive with NCO groups may contain —OH, —NH$_2$, —SH, —COOH, —NH, —CONH$_2$ and —CO—NH— groups as the reactive sites, with the proviso, of course, that such functional groups in said compound may be identical or different. Exemplary such compounds include the diols, polyols, aminoalcohols and di- and polyamines. The compound bearing the functional groups which are reactive with NCO groups may comprise an aliphatic, cyclic, cycloaliphatic or aromatic diradical; it may itself also be produced by the condensation of simple molecules and may result in a diradical comprising hetero atoms in the chain, if appropriate. Such condensates may be:

(i) polyesters produced by esterification of one or more di- or polyols with one or more di- or polyacids, or by the reaction of a cyclic lactone with a di- or polyfunctional molecule containing —OH, —NH$_2$ or —NHR groups, for example:

(ii) polyethers produced by condensation of cyclic oxides (ethylene, propylene, butylene or tetramethylene oxide) with a di— or polyfunctional molecule containing -OH, —NH$_2$ or NH groups;

(iii) mixed condensates containing polyether and polyester blocks.

These compounds are reacted with an excess of dior polyisocyanate, optionally in a solvent which is unreactive with respect to isocyanate groups. Representative such di— or polyisocyanates are:

(a) 1,3- or 1,4-diisocyanatobenzene;

(b) 2,4- or 2,6- or 2,5-diisocyanatotoluene (or alkylbenzene); and (c) 4,4'-diisocyanatodiphenylmethane, whether in pure state or containing the 2,4' and 2,2' isomers.

In the condensates under consideration, tolylene diisocyanate is most frequently employed, either in the form of the pure 2,4 isomer, or as an 80/20 or 65/35 mixture with the 2,6 isomer (TDI). Mixtures of di- or polyisocyanate can also be used.

The reaction of the excess polyisocyanate with the antagonist compound is carried out according to known means, namely, by heating admixture of both starting materials, optionally in the presence of a catalyst and/or of a solvent. Another type of condensate is that referred to as biuret and which has the following structural formula (I):

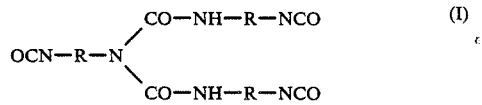

in which R is the residue of an aromatic diisocyanate.

Such condensates are produced by the reaction of water with an excess of diisocyanate. The water may be used as such, with or without a solvent. The water can also be replaced with other biuretization agents such as, in particular, tertiary alcohols, amines, formic acid and hydrogen sulfide.

Another representative type of condensate can be produced by partial cyclotrimerization of a diisocyanate under the influence of basic or organometallic catalysts, in a solvent medium where appropriate. An isocyanurate having the following structural formula (II) is thus produced:

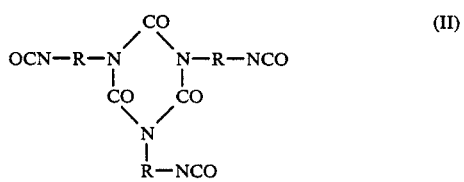

wherein R is as defined above. The catalysts which may be employed are described, for example, in *Russian Chem. Rev.*, 41, (9), pages 776 and 777 (1972), or in *Newer Methods of Preparative Organic Chemistry*. vol. VI, pages 280 to 284 (1971).

The common feature of all of these condensates containing free NCO groups is that, when the reaction is complete, they contain a more or less considerable amount of the diisocyanate employed in excess. This diisocyanate must often be removed from the resulting polycondensate, especially because of the toxicity due to the volatility of such diisocyanate. In fact, when such precondensates produced from a diisocyanate such as TDI are used, the presence of a more or less considerable amount of TDI can present substantial hazards. These hazards are very great when the precondensate is used as a thin layer, as is the case with paints and varnishes, for example, because the emission of toxic TDI vapors can become considerable and can exceed the legally permitted limits in the surrounding atmosphere.

Another undesirable situation can arise from the use of such precondensates, especially those produced by reaction of polyesters or polyethers with an excess of diisocyanate (these precondensates being most often designated prepolymers), for the manufacture of elastomeric materials, cellular or otherwise. In this case, the prepolymer is reacted with a stoichiometric amount of a reactant which is at least difunctional and which contains functional groups reactive with NCO groups, as indicated above. The final material will contain a more or less appreciable amount of the product of condensation of the excess diisocyanate with the difunctional reactant, the presence of which may adversely affect the properties of the final elastomeric material. Thus, removal of the free diisocyanate will be the only way to obtain a prepolymer having a low degree of condensation and a low free diisocyanate content at the same time.

The removal of excess diisocyanate may be carried out by known means such as evaporation, or extraction with a solvent for the diisocyanate but a nonsolvent for the condensate. However, evaporation requires the use of high temperatures, which may impair the quality of the precondensate. This disadvantage is all the more evident when the isocyanate employed is aromatic, because aromatic NCO groups are highly reactive and result, via secondary reactions when heated, in a highly viscous, or even resinous, product which can block the evaporator. Moreover, good exhaustion of the free diisocyanate requires the use of moving thin-film evaporators; these are costly devices and, in this case, require frequent stoppages and cleaning operations, because most typically the molten condensate gradually forms a resin in the apparatus. Furthermore, extraction with a solvent for the diisocyanate but which is a nonsolvent for the condensate (such as hexane, octane, etc.) is lengthy and cumbersome. In fact, as soon as the nonsolvent is added, the condensate tends to precipitate in the form of a sticky mass from which the free diisocyanate monomer is difficult to extract completely.

SUMMARY OF THE INVENTION

Accordingly, a major object of the present invention is the provision of an improved process for separating the condensate containing free NCO groups from the excess of free diisocyanate, and which improved process is easily carried out by treating (extracting) the crude condensate with an inert gas in the liquid or supercritical state. Representative such inert gases are carbon dioxide, butane, ethane, propane and ethylene. Carbon dioxide, which is cheap, nontoxic and nonflammable, is the compound of choice.

Thus, it has now unexpectedly been found not only that supercritical $CO_2$ dissolves and extracts the free diisocyanate present in the condensate, but also that the condensate remains liquid in liquid or supercritical $CO_2$ even when it is solid or resinous in consistency at the extraction temperature. This permits the condensate freed from its free diisocyanate to be subsequently transported and conveniently dissolved, and at a moderate temperature.

DETAILED DESCRIPTION OF THE PREFERRED EMBODIMENTS OF THE INVENTION

More particularly according to the present invention, the subject extraction can be carried out continuously or noncontinuously at a temperature above 31.4° C. (the critical temperature of $CO_2$) and at a pressure of from 7,300 to 50,000 kPa. The temperature preferably ranges from 31.4.° C. to 100° C. and the pressure from 7,300 to 35,000 kPa. This refers to $C_2$ in the supercritical state. In the liquid state, the $CO_2$ is used at a temperature of from 0° to 31° C. and at a pressure of 3,000 to 50,000 kPa. It is often preferable to carry out the operation at from 20° to 31° C. when the viscosity of the condensate is high. The pressure can range from 6,000 to 30,000 kPa.

The condensate containing the free diisocyanate is thus extracted with the $CO_2$ which is liquid or in the supercritical state. The operation can be carried out noncontinuously, that is to say, by mixing the condensate containing free NCO to be purified with $CO_2$ in the liquid or supercritical state in a reactor.

The reaction mass can be treated as soon as the condensation reaction has been completed.

However, bearing in mind the large amounts of excess diisocyanate monomer and, in most cases, of the solvent(s), it may be preferable and more economical to carry out, in a preliminary operation, a rapid removal of most of the excess monomeric diisocyanate, and of the solvent when the latter is present.

This treatment which is typically a very fast evaporation under reduced pressure, does not require heating to a high temperature. Therefore, it does not exhibit, or exhibits only to a very small degree, the disadvantage referred to previously, namely, producing a polymeric deposit in the apparatus which would necessitate frequent stoppages for cleaning.

In practice, therefore, the mass obtained after the condensation reaction is transferred to a thin-film evaporator which allows most of the solvent and an appreciable proportion of the excess diisocyanate monomer to be separated off.

The polyisocyanate obtained, still containing a relatively large amount of diisocyanate monomer and possibly traces of solvent, is then treated with liquid $CO_2$ or with $CO_2$ in the supercritical state.

After separation of the carbon dioxide containing the diisocyanate monomer and possibly solvent, from the purified condensate, the $CO_2$ can be separated from the extracted material by depressurizing and/or by increasing the temperature.

The extraction may be carried out in conventional manner, in apparatus which is per se known to this art.

From a source of the extraction gas (in most cases carbon dioxide), the said gas is conveyed into a heat I5 exchanger where it is liquefied. It is then transferred at the desired pressure by a pump to another heat exchanger, where it is heated to the selected extraction temperature.

The extraction gas in the liquid or supercritical state is then charged into the extraction unit which may be, for example, a column filled with a packing permitting better contact between the condensate and the extraction gas. The condensate may be introduced at the other end of the column; countercurrent extraction is then carried out. Less frequently, it may be introduced at the same end as the extraction gas; cocurrent extraction is then carried out. The purified condensate is recovered at one end of the extraction column, while the extraction gas bearing the diisocyanate monomer and possibly solvents is treated in order to separate it from the extracted materials.

This may be carried out either by lowering its pressure or by increasing its temperature, or by both lowering its pressure and increasing its temperature. These conditions are intended to modify the solvent capacity of the extraction gas.

The pressure lowering or depressurization may be performed in one or more stages, and the extraction gas may be depressurized down to a pressure equal to atmospheric pressure, or down to a higher pressure, at which point it will be recycled in the case of a continuous process.

Indeed, if the extraction gas is recycled, it is economically preferable not to depressurize it down to atmospheric pressure. This would require a greater expenditure of energy to recompress it in the cycle following the basic process. It is preferable to depressurize it down to a pressure at which the extracted compounds are not, or are very poorly, soluble.

The condensate liquefied by the extraction gas under pressure may be transported and depressurized in a vessel of sufficient capacity, in which the depressurized gas will be capable of escaping, leaving the condensate in the form of a powder or of a viscous liquid on the walls thereof. Alternatively, the condensate liquefied by the extraction gas may be received in a solvent or in a mixture of solvents which, after depressurization, yields a condensate solution ready for use.

As indicated above, the process can be carried out continuously or noncontinuously, and the apparatus employed is not to be considered as being limited to the principle of operation described earlier.

It is generally preferable according to the process of the invention, to employ the extraction gas in the supercritical state.

In order to further illustrate the present invention and the advantages thereof, the following specific examples are given, it being understood that same are intended only as illustrative and in nowise limitative.

EXAMPLE 1

1,044 g of TDI (toluene diisocyanate, 80/20 mixture of the 2,4 and 2,6 isomers) and 210 g of acetone were charged into a 2-liter three-necked round-bottomed flask fitted with a stirrer, a condenser, an oil heating bath and a dropping funnel.

The solution was heated to 45° C. and a solution of 14.4 g of water in 40 g of acetone was introduced therein over 1 hour with the condenser in the reflux position. The condenser was then fitted in the distillation position (external condensation) and the temperature was raised to 145° C. over 3 hours. It was maintained at 145° C. for 1 hour with a nitrogen purge which removed most of the remaining acetone.

A solution of TDI biuret in excess TDI was obtained (after cooling), and was found by titration to contain 0.940 NCO groups per 100 g. This solution consisted of ⅔ free TDI and ⅓ of TDI biuret and its higher homologs.

Extraction No. 1 (liquid $CO_2$):

26.65 g of the TDI +TDI biuret solution obtained above were charged into a 50-$cm^3$ pressure-resistant reactor.

The $CO_2$ was injected at 8,000 kPa and at 20° C., at a rate of 1 kg/hour.

After 45 minutes, 14.14 g of product consisting of 92% of TDI and 8% of biuret had been extracted (after removal of $CO_2$)

After a second period of 45 minutes, an additional 1.35 g of product consisting of 97% of TDI and 3% of biuret were extracted (after removal of $C_2$).

The remaining product can be withdrawn from the reactor: it was, in fact, in the form of a viscous liquid (under pressure).

On depressurization in a bottle, a slightly yellow white powder containing 10 to 12% of free TDI was obtained.

Extraction No. 2 (supercritical $CO_2$)

An extraction of 27.48 g of the same product as in Extraction No. 1 was carried out in the same apparatus, with $CO_2$ at 50° C. and at 120 - 190 bars, in the following manner:

(i) 45 minutes at 12,000 kPa ($CO_2$ flow rate=1 kg/hour), yielding 11.17 g of extracted product after depressurization;

(ii) 48 minutes at 19,000 kPa ($CO_2$ flow rate=1 kg/hour), yielding 4.43 g of extracted product after depressurization;

(iii) 15 minutes at 19,000 kPa ($CO_2$ flow rate=1 kg/hour), yielding 0.1 g of extracted product after depressurization.

The total weight of the extracts was 15.7 g, containing 95% of TDI and 5% of biuret.

The remaining product, pressurized in a bottle, was deposited therein in the form of a powder. 8.5 g of a solid containing 5% of TDI and 95% of biuret were obtained in this manner.

EXAMPLE 2

200 g of polyester and 34.8 g of TDI (toluene diisocyanate, 80/20 mixture of 2,4 and 2,6 isomers) were charged into a reactor with a stirrer and with heating by means of an oil bath. The polyester was a polyethylene polyadipate, with hydroxyl end groups and a molecular weight of 2,000, containing 0.100 OH/100 g.

After heating to 80°-90° C. for 1 h, 30 min, a prepolymer containing free NCO groups and found by titration to contain 3% of free TDI monomer was obtained.

23.5 g of prepolymer were placed in the extraction apparatus described in Example 1, and $CO_2$ was injected at 19,000 kPa at 50° C. for 45 minutes at a rate of 1 kg/hour.

The residue obtained after depressurization of $CO_2$ was determined by titration to contain 0.5% of free TDI.

An extraction was carried out on 38.5 g of prepolymer, the $CO_2$ being at 78° C. at 18,600 kPa (flow rate 1 kg/hour) for 55 minutes.

After depressurization, the prepolymer extracted was determined by titration to contain less than 1,000 ppm of free TDI.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed:

1. A process for the purification and isolation of an isocyanate condensate containing free NCO groups from an impure admixture thereof, said isocyanate condensate impure admixture having been prepared by reacting a stoichiometric excess of an aromatic di- or polyisocyanate with a reactant compound containing at least two functional groups which are reactive with NCO groups, and comprising extracting unreacted excess di- or polyisocyanate from said impure admixture with an inert gas in either the liquid or supercritical state.

2. The process as defined by claim 1, said reactant compound comprising an aromatic diisocyanate.

3. The process as defined by claim 1, said aromatic di- or polyisocyanate comprising 1,3-diisocyanatobenzene, 1,4-diisocyanatobenzene, 2,4-diisocyanatotoluene, 2,6-diisocyanatotoluene, 2,5-diisocyanatotoluene, 4,4'-diisocyanatodiphenylmethane, 2,4'-diisocyanatodiphenylmethane, or 2,2'-diisocyanatodiphenylmethane.

4. The process as defined by claim 3, said aromatic di- or polyisocyanate comprising 2,4-diisocyanatotoluene, or mixture thereof with 2,6-diisocyanatotoluene.

5. The process as defined by claim 1, said reactant compound comprising water.

6. The process as defined by claim 1, said reactant compound comprising a polyester, polyether or mixed polyether/polyester condensate.

7. The process as defined by claim 1, said inert gas in either the liquid or supercritical state comprising carbon dioxide.

8. The process as defined by claim 7, carried out at a temperature of from 0° to 31° C. and at a pressure of from 3,000 to 50,000 kPa.

9. The process as defined by claim 8, carried out at a temperature of from 0° to 31°C. and at a pressure of from 6,000 to 30,000 kPa.

10. The process as defined by claim 7, carried out at a temperature above the critical temperature of carbon dioxide.

11. The process as defined by claim 10, carried out at a temperature below 100° C. and at a pressure of from 7,300 to 50,000 kPa.

12. The process as defined by claim 1, carried out at a pressure of from 7,300 to 35,000 kPa.

13. The process as defined by claim 1, carried out in the presence of an NCO inert solvent reaction medium.

14. The process as defined by claim 1, comprising preliminarily removing a substantial fraction of the unreacted excess di- or polyisocyanate prior to extracting with said inert gas in liquid or supercritical state.

15. The process as defined by claim 14, said preliminary removal comprising an evaporation stage.

16. The process as defined by claim 1, said inert gas in either the liquid or supercritical state comprising butane, ethane, propane or ethylene.

17. The process as defined by claim 1, said inert gas being in supercritical state.

18. The process as defined by claim 1, said inert gas being in liquid state.

19. The product of the process as defined by claim 1.

* * * * *